US009804106B2

(12) United States Patent
Rothe

(10) Patent No.: US 9,804,106 B2
(45) Date of Patent: Oct. 31, 2017

(54) IMAGING SYSTEM AND METHOD WITH SCATTER CORRECTION

(71) Applicant: General Electric Company, Schenectady, NY (US)

(72) Inventor: Nils Rothe, Hannover (DE)

(73) Assignee: General Electric Company, Schenectady, NY (US)

( * ) Notice: Subject to any disclaimer, the term of this patent is extended or adjusted under 35 U.S.C. 154(b) by 225 days.

(21) Appl. No.: 14/854,663

(22) Filed: Sep. 15, 2015

(65) Prior Publication Data

US 2016/0258885 A1 Sep. 8, 2016

Related U.S. Application Data

(63) Continuation-in-part of application No. PCT/EP2015/054737, filed on Mar. 6, 2015.

(51) Int. Cl.
*A61B 6/03* (2006.01)
*G01N 23/04* (2006.01)
(Continued)

(52) U.S. Cl.
CPC ........... *G01N 23/046* (2013.01); *A61B 6/032* (2013.01); *A61B 6/5282* (2013.01);
(Continued)

(58) Field of Classification Search
CPC ......... A61B 6/032; A61B 6/06; A61B 6/4291; A61B 6/483; A61B 6/5235; A61B 6/5258;
(Continued)

(56) References Cited

U.S. PATENT DOCUMENTS 6,175,609 B1 * 1/2001 Edic ..................... G01N 23/046
378/155
6,339,636 B1 * 1/2002 Ogawa .................. A61B 6/032
378/146

(Continued)

FOREIGN PATENT DOCUMENTS

| GB | 1352888 A | 5/1974 |
| WO | 0157882 A1 | 8/2001 |
| WO | 33073377 A2 | 9/2003 |

OTHER PUBLICATIONS

PCT Search Report and Written Opinion issued in connection with Related PCT Application No. PCT/EP2015/054737 dated May 12, 2015.
PCT Search Report and Written Opinion issued in connection with corresponding PCT Application No. PCT/US2016/050410 dated Nov. 28, 2016.

*Primary Examiner* — Thomas R Artman
(74) *Attorney, Agent, or Firm* — Barclay Damon LLP

(57) ABSTRACT

A method and system for imaging an object are described herein. A scatter image of the object is generated at a projection angle. In generating the scatter image, a non-grid image of the object is acquired using a radiation source and a detector. An aperture plate is positioned between the object and the detector and a first grid image of the object is acquired. The aperture plate includes a plurality of apertures positioned on a grid. The aperture plate is moved to a second position and a second grid image of the object is acquired. A scatter image of the object is generated based on the non-grid image, the first grid image, and the second grid image and stored.

20 Claims, 13 Drawing Sheets

(51) Int. Cl.
*A61B 6/00* (2006.01)
*G21K 1/02* (2006.01)

(52) U.S. Cl.
CPC . *G01N 2223/051* (2013.01); *G01N 2223/316* (2013.01); *G21K 1/02* (2013.01)

(58) Field of Classification Search
CPC .... A61B 6/5282; G01N 23/04; G01N 23/046; G01N 23/06; G01N 23/083; G01N 23/20083; G01N 2223/051; G01N 2223/055; G01N 2223/316; G01N 2223/32; G01N 2223/321; G21K 1/02; G21K 1/025; G21K 1/10; G21K 1/12
See application file for complete search history.

(56) References Cited

U.S. PATENT DOCUMENTS

| | | | |
|---|---|---|---|
| 6,408,049 B1 | 6/2002 | Edic et al. | |
| 7,570,732 B2 * | 8/2009 | Stanton | A61B 6/02 378/7 |
| 7,785,098 B1 | 8/2010 | Appleby et al. | |
| 8,184,767 B2 * | 5/2012 | Mishra | H04N 5/32 378/154 |
| 2005/0213701 A1 | 9/2005 | Sendai | |
| 2007/0127621 A1 * | 6/2007 | Grass | A61B 6/032 378/4 |
| 2007/0242794 A1 * | 10/2007 | Stanton | A61B 6/02 378/5 |
| 2010/0140485 A1 * | 6/2010 | Mishra | H04N 5/32 250/363.1 |
| 2016/0258885 A1 * | 9/2016 | Rothe | G01N 23/046 |

* cited by examiner

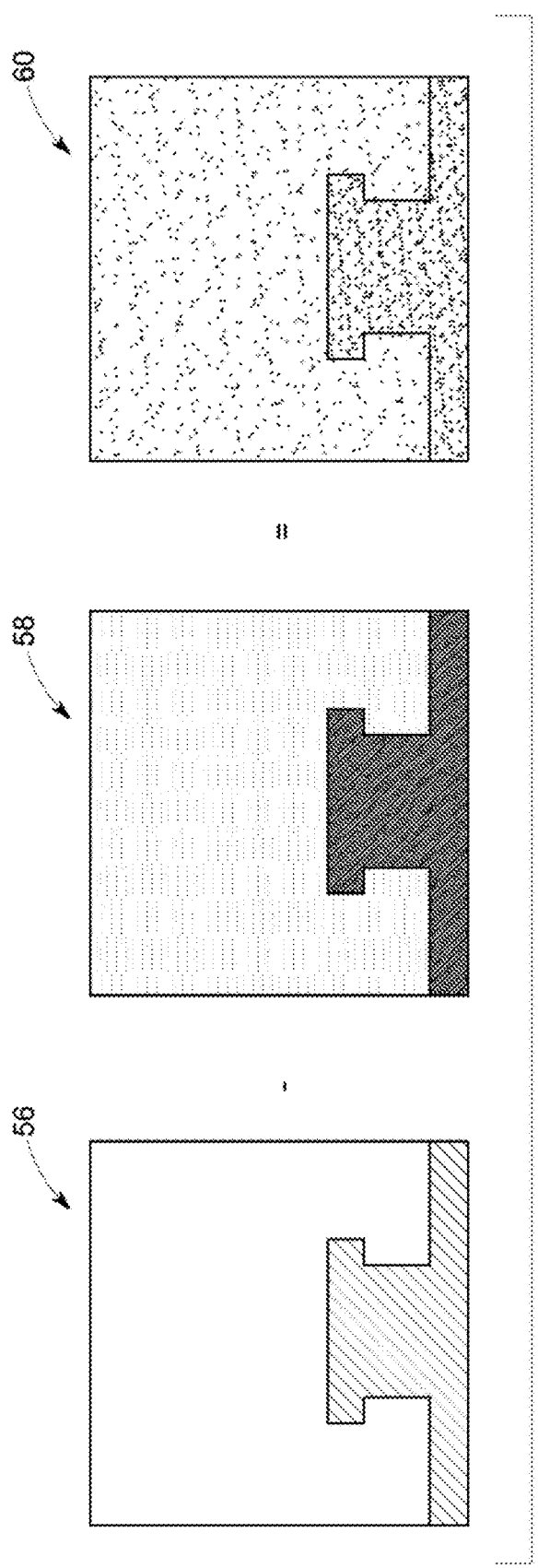

IMAGING SYSTEM AND METHOD WITH SCATTER CORRECTION

CROSS REFERENCE TO RELATED APPLICATIONS

This application is a Continuation-in-Part of, and claims priority to, International Patent Application Serial No. PCT/EP2015/054737, filed Mar. 6, 2015, and entitled IMAGING SYSTEM AND METHOD WITH SCATTER CORRECTION, the entirety of which is incorporated herein by reference.

BACKGROUND

The subject matter disclosed herein relates generally to the field of non-invasive imaging and more specifically to the field of computed tomography (CT) imaging and inspection systems. In particular, the subject matter disclosed herein relates to a technique for correcting scatter from digital radiographs acquired via volumetric computed tomography (VCT) systems.

Inspection of objects is of vital importance in manufacturing and repair industries. Various types of inspection systems, such as computed tomography (CT), coordinate measuring machines (CMM), laser-based profilometry, light gauge, infrared and others, are used in industrial inspection processes for a wide variety of applications. For example, these inspection systems may be used for measuring dimensions or for identifying defects in manufactured parts, such as turbine blades. Each of these inspection systems has its advantages and disadvantages. Modalities such as CMM and laser-based profilometry typically measure external surfaces with high accuracy, but cannot measure internal features unless the object is cut open. To date, CT is the most versatile of the measurement/inspection systems for revealing both the internal and external structures of industrial parts in a non-destructive manner. Because of their ability to provide internal as well as external measurements, CT based techniques may facilitate processes such as reverse engineering, rapid prototyping, casting simulation and validation, tire development, first article inspection, ceramic porosity inspection, process validation, parts qualification and defect detection, among others. However, CT based techniques may also have certain limitations, which may deter their widespread use.

For example, volumetric computerized tomography (VCT) imaging for industrial applications (e.g., imaging of metallic parts) typically provides unsatisfactory images having image artifacts due to radiation-matter interaction based artifacts, scanner based artifacts, reconstruction techniques based artifacts, and so forth. The radiation-matter interaction based artifacts may further include beam hardening artifacts and artifacts due to x-ray scatter radiations. Scatter radiation in the projection images reduces the contrast of the projection images, produces degradation of or blurs sharp features of the object in the generated volume images, and reduces the accuracy of metrology applications and the detectability of smaller features. Scatter radiation is a strong function of the imaging parameters such as the object under imaging, beam spectrum used, geometrical distances, and the surrounding medium. Due to various dependencies in the imaging parameters, an accurate estimation of the scatter signal content in projection imaging is challenging. Physics-based models are often used for predicting scatter content in x-ray images, however they are time consuming and predict only scatter arising out of the object under scanning, provided the material properties are known.

There exist different techniques for scatter measurement and scatter correction in acquired projection images. For example, one popular scatter measurement technique employs a beam stopper located between the radiation source and the object being scanned in a VCT system to measure the scatter at a corresponding location. However, most currently known techniques primarily address the object scatter and involve time-consuming computer simulations.

As manufacturing tolerances become tighter, there is a corresponding increase in the demands for metrology techniques for maintaining the tolerances. The need for quality and performance testing has become an integral part of the production or manufacturing process. Thus, in order to improve CT inspection accuracy and efficiency, more effective methods are needed for removing scatter radiation related artifacts.

In order to improve image quality, a scatter rejecting aperture plate can be positioned between the object being imaged and the detector. This aperture plate reduces scatter and thus improves quality of the generated images. However, fine structures on the object between the apertures of the aperture plate can produce artifacts after scatter correction.

SUMMARY

A method and system for imaging an object are described herein. A scatter image of the object is generated at a projection angle. In generating the scatter image, a non-grid image of the object is acquired using a radiation source and a detector. A scatter rejecting aperture plate is positioned between the object and the detector and a first grid image of the object is acquired. The scatter rejecting aperture plate includes a plurality of apertures positioned on a grid. The scatter rejecting aperture plate is moved to a second position and a second grid image of the object is acquired. A scatter image of the object is generated based on the non-grid image, the first grid image, and the second grid image and stored.

In an embodiment, a method for generating a scatter image of an object at a projection angle in an imaging system is described. The method includes acquiring a non-grid image of the object using a radiation source and a detector and positioning a scatter rejecting aperture plate between the object and the detector at a first position. The scatter rejecting aperture plate includes a plurality of apertures, said apertures being positioned on a grid. A first grid image of the object is acquired with the scatter rejecting aperture plate disposed between the object and the detector at the first position. The scatter rejecting aperture plate is moved to a second position between the object and the detector and a second grid image of the object is acquired with the scatter rejecting aperture plate disposed between the object and the detector at the second position. A scatter image of the object is generated based on the non-grid image, the first grid image, and the second grid image and is stored.

In another embodiment, a method for generating a three-dimensional image of an object is described. The method includes acquiring a plurality of projection images of the object using a source and a detector oriented at a plurality of projection angles relative to the object. The plurality of projection angles is realized by relatively rotating the object and the radiation source in a common plane of rotation. A scatter image is acquired at each of the plurality of projection angles. Acquiring each scatter image includes acquiring a non-grid image of the object using a radiation source and a detector, positioning a scatter rejecting aperture plate between the object and the detector at a first position, and acquiring a first grid image of the object with the scatter rejecting aperture plate disposed between the object and the detector at the first position. The scatter rejecting aperture plate includes a plurality of apertures, the aperture being positioned on a grid. The scatter rejecting aperture plate is moved to a second position between the object and the detector and a second grid image of the object is acquired with the scatter rejecting aperture plate disposed between the object and the detector at the second position. The scatter image of the object is generated based on the non-grid image, the first grid image, and the second grid image. A plurality of scatter free projection images is generated by correcting the plurality of projection images based on respective ones of a plurality of stored scatter images by subtracting the scatter images from the respective projection images in a single process step and reconstructing a three-dimensional image of the object based on the scatter free projection images.

In a further embodiment, a volumetric CT system for imaging an object is described. The CT system is configured to generate a scatter free image of an object for use in generating a three-dimensional image of the object. The system includes a source and a detector configured to move with respect to the object, the detector configured to acquire a plurality of images of the object. A scatter rejecting aperture plate is configured to be positioned at a plurality of positions between the object and the detector. The scatter rejecting aperture plate includes a plurality of apertures, the aperture positioned on a grid. A processor is configured to acquire a non-grid image of the object without the scatter rejecting aperture plate and a grid image of the object with the aperture plate at each of the plurality of positions between the object and the detector and generate the scatter image of the object based on the non-grid image and the grid images acquired at each of the plurality of positions.

The above embodiments are exemplary only. Other embodiments are within the scope of the disclosed subject matter.

BRIEF DESCRIPTION OF THE DRAWINGS

So that the manner in which the features of the subject matter disclosed herein can be understood, a detailed description of the disclosed subject matter may be had by reference to certain embodiments, some of which are illustrated in the accompanying drawings. It is to be noted, however, that the drawings illustrate only certain embodiments of the disclosed subject matter and are therefore not to be considered limiting of its scope, for the scope of the disclosed subject matter encompasses embodiments as well. The drawings are not necessarily to scale, emphasis generally being placed upon illustrating the features of certain embodiments of the disclosed subject matter. In the drawings, like numerals are used to indicate like parts throughout the various views.

FIG. 5 depicts a schematic for generating a scatter grid image by employing the scatter rejection plate of FIG. 2 in accordance with aspects of the present technique;

DETAILED DESCRIPTION

The present techniques are generally directed to computed tomography (CT) imaging resulting in improved image quality. Such imaging techniques may be useful in a variety of imaging contexts, such as medical imaging, industrial metrology and inspection, security screening, baggage or package inspection, and so forth. Moreover, such imaging techniques may be employed in a variety of imaging systems, such as CT systems, tomosynthesis systems, X-ray imaging systems, and so forth. Though the present discussion provides examples in an industrial inspection context with respect to CT systems resulting in improved measurement and inspection accuracy, one of ordinary skill in the art will readily apprehend that the application of these techniques in other contexts and in other systems is well within the scope of the present techniques.

Figure 1:
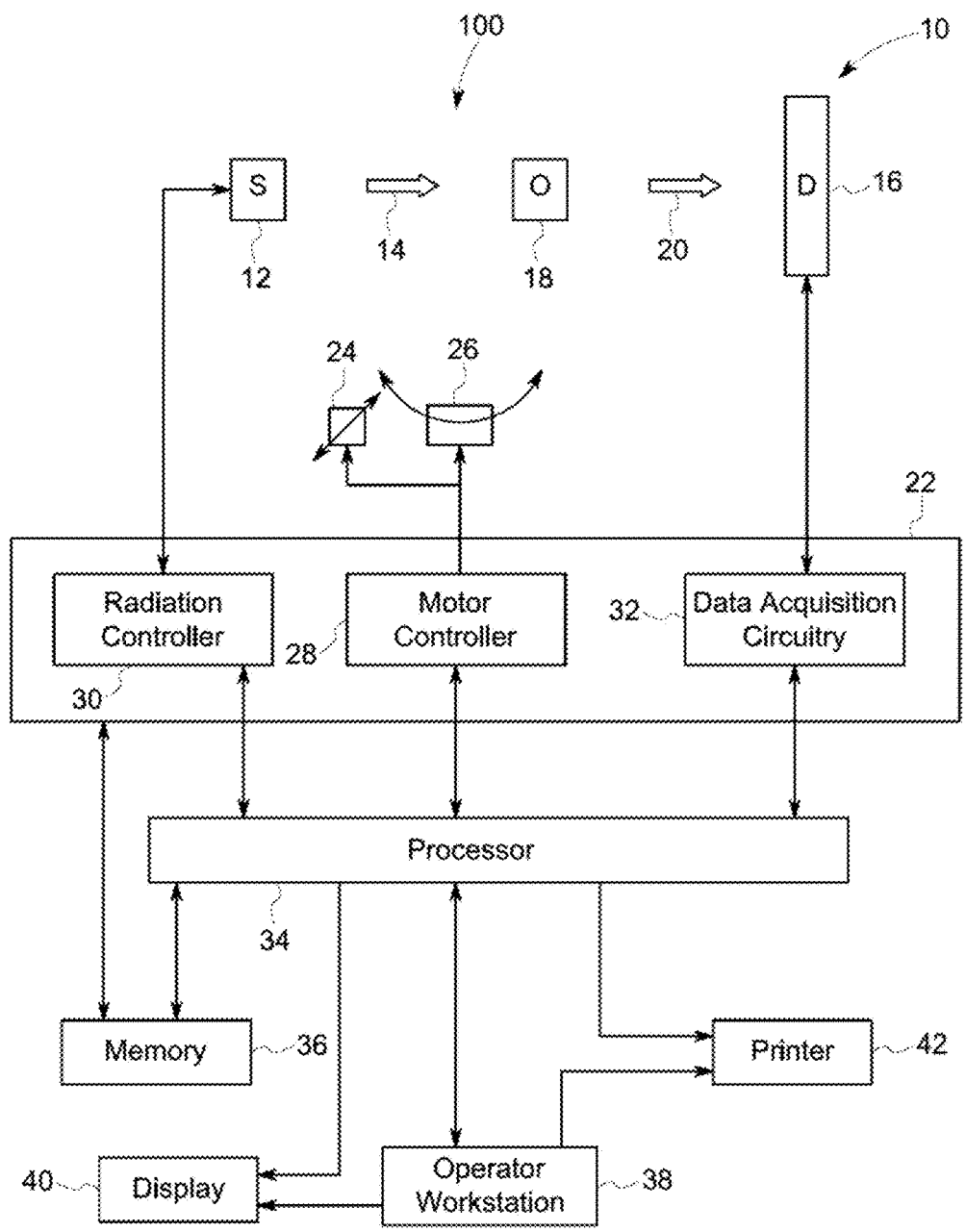
FIG. 1 depicts an exemplary flat panel VCT system for imaging an object in which aspects of the present technique may be practiced.

Referring now to FIG. 1, an imaging system 10 for use in accordance with the present technique is illustrated. In the illustrated embodiment, the imaging system 10 can be a volumetric computed tomography (VCT) system designed both to acquire image data and to process the image data for display and analysis in accordance with the present technique. In the illustrated embodiment, the imaging system 10 can include a radiation source 12, such as an X-ray source. A collimator may be positioned adjacent to the radiation source 12 for regulating the size and shape of a stream of radiation 14 that emerges from the radiation source 12.

In typical operation, the radiation source 12 projects a stream of radiation 14, such as an X-ray beam, towards a detector array 16 placed on the opposite side of the radiation source 12, relative to the imaged object. The stream of radiation 14 passes into an imaging volume in which an object 18, such as a turbine blade or other item to be imaged may be positioned. Non-limiting examples of the object 12 include industrial parts, including but not limited to turbine airfoils, blades, disks, and shafts. It should be noted that a particular region of the object 18 may be chosen by an operator for imaging so that the most useful scan of the region may be acquired.

A portion of the radiation 20 passes through or around the object 18 and impacts the detector array 16. The detector array 16 may be an area detector and can be generally formed as a two-dimensional array of detection elements. In one implementation, the detector array 16 may be a flat-panel detector formed as rows and columns of detector elements that may be individually read out. Each detector element produces an electrical signal that represents the intensity of the incident radiation 20 at the detector element when the radiation 20 strikes the detector array 16. Typically, signals can be acquired at one or more view angle positions around the object 18 so that a plurality of radiographic views may be collected. These signals can be acquired and processed to reconstruct an image of the features internal as well as external to the object 18.

The object 18, the radiation source 12, and the detector array 16 can be typically displaced relative to each other, allowing projection data to be acquired at various views relative to the object 18 if desired. For example, in one implementation, the object 18 may be positioned on a table, such as a turntable, so that the object 18 may be rotated in a common plane of rotation 100 during the examination process to expose the object 18 to the stream of radiation 14 from all sides. Alternatively, the radiation source 12 and/or the detector array 16 may be disposed on a gantry, which may be rotated around the object 18 placed on a table during the examination process. Further, in certain embodiments, components of the imaging system as well as the imaged object may be moved during the examination process to acquire projection images at different views. As the object 18 and the radiation source 12 rotate relative to each other in a common plane of rotation 100, the detector array 16 collects data of radiation attenuation at the various view angles relative to the object 18.

Data collected from the detector array 16 then typically undergoes pre-processing to condition the data to represent the line integrals of the attenuation coefficients of the scanned objects 18. The processed data, commonly called projections, can then be reconstructed to formulate a volumetric image of the scanned area, as discussed in greater detail below.

Operation of the source 12 can be controlled by a system controller 22, which furnishes both power, and control signals for examination sequences. Moreover, the detector array 16 can be coupled to the system controller 22, which commands acquisition of the signals generated in the detector array 16. The system controller 22 may also execute various signal processing and filtration functions, such as for initial adjustment of dynamic ranges, interleaving of digital image data, and so forth. In general, the system controller 22 commands operation of the imaging system 10 to execute examination protocols and to process acquired data. In the present context, system controller 22 may also include signal processing circuitry and other circuitry, typically based upon a general purpose or application-specific digital computer, with associated memory circuitry. The associated memory circuitry may store programs and routines executed by the computer, configuration parameters, image data, and so forth. For example, the associated memory circuitry may store programs or routines for implementing the present technique.

In the embodiment illustrated in FIG. 1, the system controller 22 can be coupled to a linear positioning subsystem 24 and a rotational subsystem 26. In particular, the system controller 22 may include a motor controller 28 that controls the operation of the linear positioning subsystem 24 and the rotational subsystem 26. The rotational subsystem 26 enables the X-ray source assembly and/or the detector assembly to be rotated around the object or the patient 18. It should be noted that the rotational subsystem 26 may include a gantry. Thus, the system controller 22 may be utilized to control the rotational speed and position of the gantry. Alternatively, the rotational subsystem 26 may include a motorized turntable and the system controller 22 may be configured to rotate the motorized turntable, thereby rotating the object 18 one or multiple turns during an examination. The linear positioning subsystem 24 enables the object 18 to be displaced linearly, such as by moving a table or support on which the object 18 rests. Thus, in one embodiment, the table may be linearly moved within a gantry to generate images of particular areas of the object 18. In another embodiment (e.g., in a tomosynthesis system), the X-ray source may be moveable using a linear positioning subsystem. The detector position may be variable, but not be controlled using a positioning subsystem. It should be noted that other configurations may also be used.

Additionally, as will be appreciated by those skilled in the art, the radiation source 12 may be controlled by a radiation controller 30 disposed within the system controller 22. Particularly, the radiation controller 30 may be configured to provide power and timing signals to the radiation source 12. Further, the system controller 22 may include data acquisition circuitry 32. In this exemplary embodiment, the detector array 16 can be coupled to the system controller 22, and more particularly to the data acquisition circuitry 32. The data acquisition circuitry 32 typically receives sampled analog signals from the detector array 16 and converts the data to digital signals for subsequent processing by a processor 34. Such conversion, and indeed any preprocessing, may actually be performed to some degree within the detector assembly itself.

The processor 34 can be typically coupled to the system controller 22. Data collected by the data acquisition circuitry 32 may be transmitted to the processor 34 for subsequent processing and reconstruction. Reconstruction of the image may be done by general or special purpose circuitry of the processor 34. Once reconstructed, the image produced by the imaging system 10 reveals internal as well as external features of the object 18. Alternatively, an image reconstruction that can be coupled to or can be a part of a processor 34, may receive sampled and digitized data from the data acquisition circuitry 32 and may perform high-speed image reconstruction to generate one or more images of the scanned object 18.

The processor 34 may include or be in communication with a memory 36. It should be understood that any type of computer accessible memory device suitable for storing and/or processing such data and/or data processing routines may be utilized by such an exemplary imaging system 10. Moreover, the memory 36 may comprise one or more memory devices, such as magnetic or optical devices, of similar or different types, which may be local and/or remote to the system 10. The memory 36 may store data, processing parameters, and/or computer programs comprising one or more routines for performing the processes described herein. Furthermore, memory 36 may be coupled directly to system controller 24 to facilitate the storage of acquired data.

The processor 34 can be typically used to control the imaging system 10. The processor 34 may also be adapted to control features enabled by the system controller 22, i.e., scanning operations and data acquisition. Indeed, the system controller 22 may be implemented as hardware and software components of the depicted processor 34. In addition, the processor 34 may be configured to receive commands and scanning parameters from an operator via an operator workstation 38. For example, the operator workstation 38 may be equipped with a keyboard and/or other input devices by which an operator may control the imaging system 10. Thus, the operator may observe the reconstructed image and other data relevant to the system from processor 34, initiate imaging and so forth. Where desired, other computers or workstations may perform some or all of the functions of the present technique, including post-processing of image data simply accessed from memory device 36 or another memory device at the imaging system location or remote from that location.

A display 40 may be coupled to one of the operator workstation 38 and the processor 34 and may be utilized to observe the reconstructed image and/or to control imaging. Additionally, the scanned image may also be printed by a printer 42 which may be coupled to the processor 34 and/or the operator workstation 38, either directly or over a network. It should be further noted that the processor 34 and/or operator workstation 38 may be coupled to other output devices that may include standard or special purpose computer monitors and associated processing circuitry. Furthermore, additional operator workstations may be further linked in the imaging system 10 for outputting system parameters, requesting inspection, viewing images, and so forth, so that more than one operator may perform operations related to the imaging system 10. For example, one operator may utilize one operator workstation to image acquisition while a second operator utilizes a second operator workstation to reconstruct and/or review the results of the imaging routines. In general, displays, printers, workstations, and similar devices supplied within the imaging system 10 may be local to the data acquisition components, or may be remote from these components linked to the imaging system 10 via one or more configurable networks, such as the Internet, virtual private networks, and so forth.

The exemplary imaging system 10, as well as other imaging systems based on radiation attenuation, may employ a variety of scatter mitigation and/or correction techniques for improving the image quality. For example, the present technique employs a scatter rejecting aperture plate, depicted in FIG. 2 and represented generally at reference numeral 46, for rejecting the scatter radiation resulting from object as well as those resulting from the background in accordance with aspects of the present technique.

Figure 2:
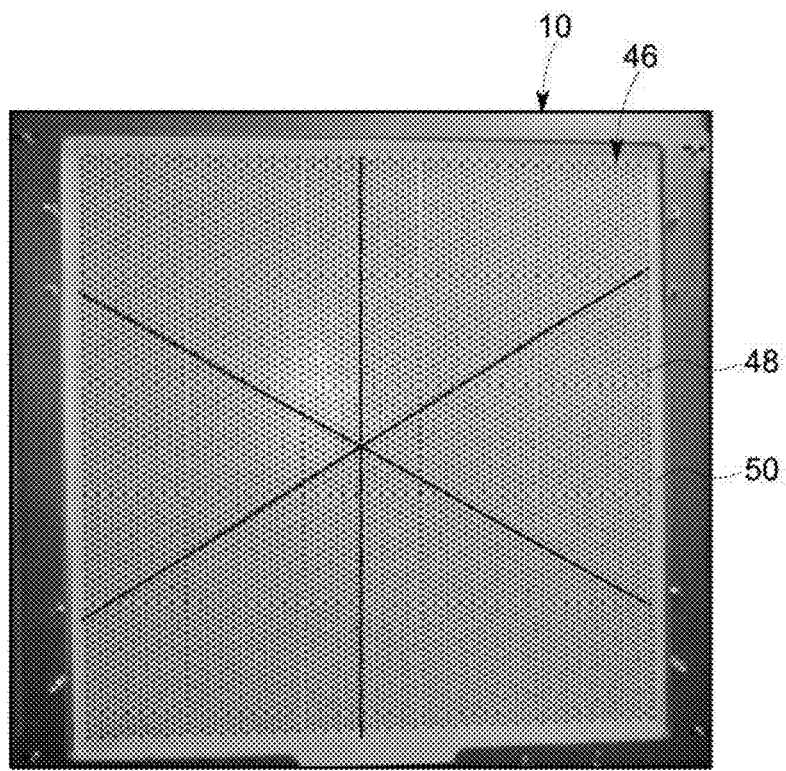
FIG. 2 depicts a scatter rejection plate in accordance with aspects of the present technique for use in flat panel VCT system of FIG. 1.

The aperture plate 46, as illustrated in FIG. 2, can include a plurality of sub-centimeter sized circular apertures 48 drilled in a plate 50. It is to be understood that the apertures 48 are shown to be circular by way of example only as circular apertures can be easily manufactured by conventional mechanical drilling. However, using other manufacturing methods like laser drilling apertures with different shapes can be produced. More particularly apertures with regular geometric shapes like triangular, rectangular, hexagonal or octagonal become available. Further even less regular shapes like elliptic or even freely formed apertures become available.

Figure 3:
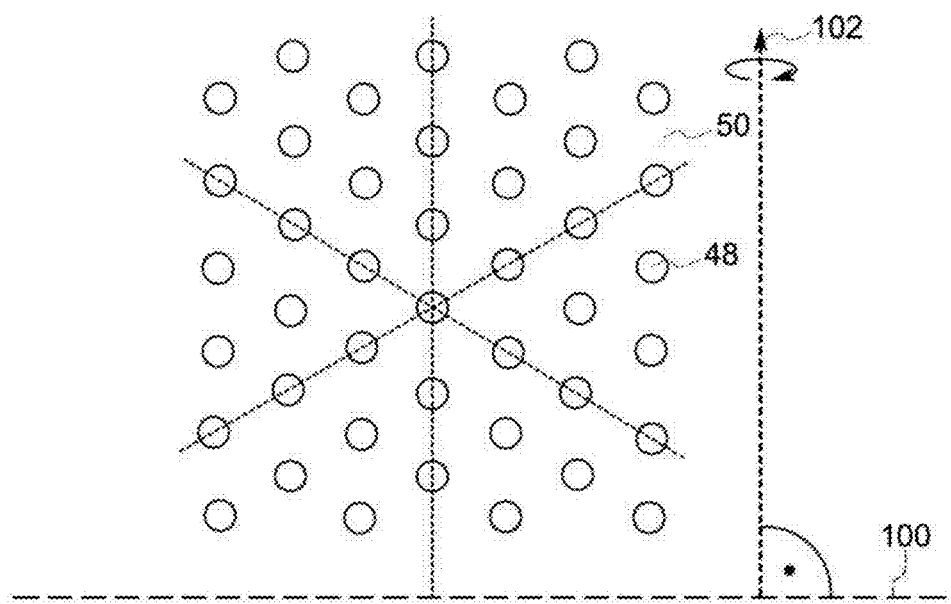
FIG. 3 depicts an enlarged view of the scatter rejection plate of FIG. 2.

The circular apertures 48 of the preferred embodiment shown in FIGS. 2 and 3 can be positioned on a two-dimensional hexagonal grid to optimize the packaging density of the apertures 48 whilst keeping the distance between next neighbors at a level which has been found best suited in the imaging system known from U.S. Pat. No. 8,184,767 B2. The grid lines (dotted lines) have been indicated for reason of clarity. In certain embodiments, the circular apertures 48 may be about 1-2 millimeters in diameter spaced apart at about 5 millimeters from each other (center-to-center).

In general terms the apertures 48 have a diameter and a next-neighbor distance. It has been found as a general rule that preferably the ratio between next-neighbor distance and diameter can be in the range of 2 and 3. In a particular embodiment the ratio can be about 2.5. By way of example, circular apertures 48 having a diameter of 1 millimeter can be preferably placed on a hexagonal grid with a next-neighbor distance of about 2.5 millimeters. The exact ratio depends on a number of parameters including, but not limited to, the features of the x-ray flat panel detector. Therefore it is to be understood that the ratio of 2.5 may need some adjustment to meet the requirements of the equipment that causes the unwanted x-ray scattering.

The enhanced density of the apertures 48 placed on a hexagonal grid with unaltered next-neighbor distance minimizes the area in images acquired with the aperture plate 46 in place in which image information cannot be acquired by x-ray but needs to be computed based on a suited interpolating algorithm. This results in a higher quality of the images acquired with the aperture plate 46 in place compared to prior art. Typically, the plate 50 can be thick and made of high-density material. The high-density material may be, for example, lead, tungsten or a tungsten alloy, molybdenum, tantalum or rhenium. In certain embodiments, the plate can be about 10 to 20 millimeters in thickness. In certain embodiments, the plate 50 can be made of lead and can be about 19 millimeters in thickness.

FIG. 3 shows an enlarged view of the aperture plate 46 as shown in FIG. 2. From FIG. 3 the two-dimensional hexagonal grid is apparent. Again the grid lines (dotted lines) have been indicated for reason of clarity. Additionally surface normal 102 of the common plane of relative rotation 100 of object 18 and the radiation source 12 has been indicated in FIG. 3.

Figure 4A:
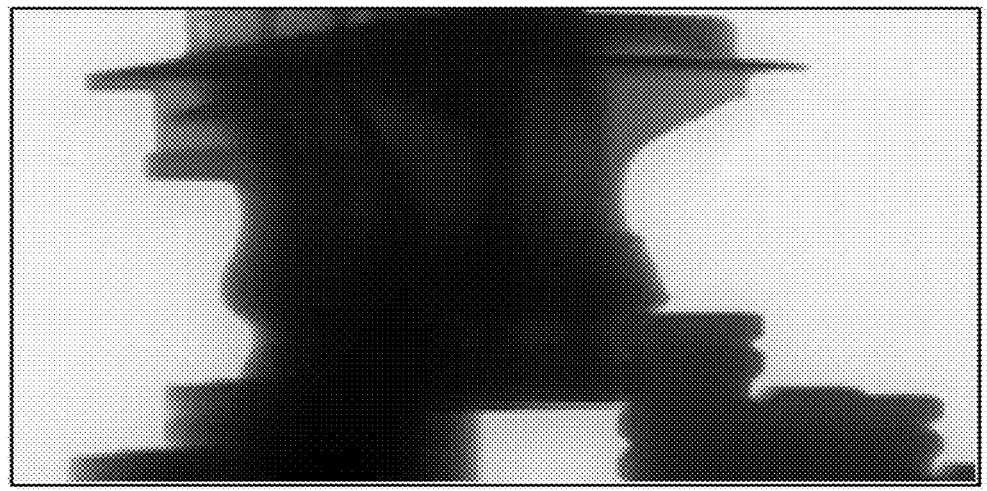
FIGS. 4A-4D depict, for a turbine fan blade, two uncorrected images, one scatter corrected image and one reconstructed volumetric image data image by employing the method pursuant to U.S. Pat. No. 8,184,767 B2.
Figure 4B:
Figure 4C:
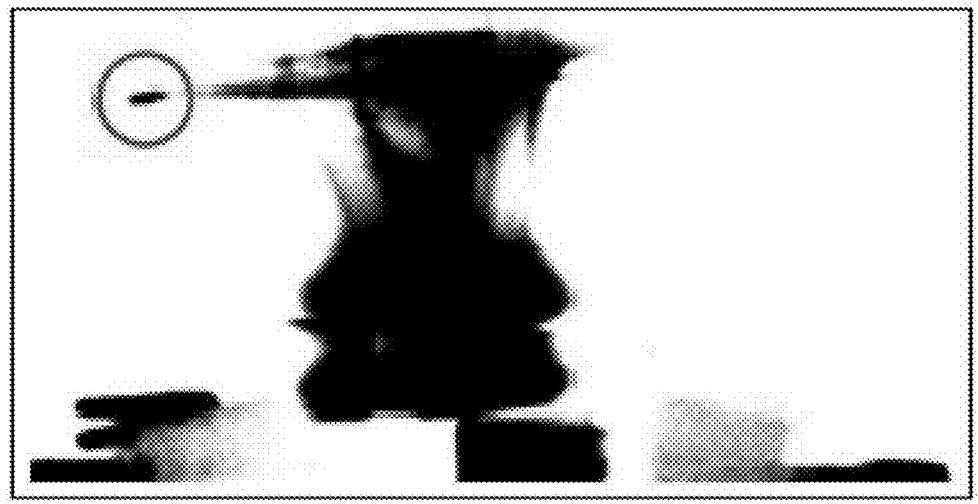
Figure 4D:

Whilst the x-ray inspection method according to U.S. Pat. No. 8,184,767 B2 allows for minimizing the effect of x-ray radiation scattered in the x-ray detection equipment the method at the same time can induce artifacts in scatter corrected images. These artifacts can also negatively affect the quality of volume data reconstructed from scatter corrected images by means of VCT. I.e. if a rectangular grid is employed for the method and the orientation of the rectangular grid relative to the common plane of relative rotation of object 18 and the radiation source 12 is such that one of the grid lines is parallel to the surface normal of the common plane of rotation specific areas of object 18 can be covered by the aperture plate 46 for all acquisition angles. Thus no X-ray attenuation information relating to these areas can be collected by direct measurement but needs to be calculated by appropriate interpolating methods. These methods however cannot account for small structures located in said areas. In fact in this case these structures can be partly to fully masked in the acquired images. Hence they cannot properly appear in any scatter corrected images or, consequently, in any volumetric image reconstructed therefrom. The inventors recognized that even worse the same effect can also cause severe artifacts in volumetric image data reconstructed from scatter corrected images generated pursuant to the teaching of U.S. Pat. No. 8,184,767 B2. This effect is illustrated by means of FIG. 4. FIGS. 4A to 4D which depict, for a turbine fan blade, two uncorrected images acquired at two different acquisition angles A (FIG. 4A) and B (FIG. 4B), the image acquired at acquisition angle B with scatter correction applied employing the method pursuant to U.S. Pat. No. 8,184,767 B2 (FIG. 4C) and finally volumetric image data of the turbine fan blade reconstructed from the multiple acquired and scatter corrected images (FIG. 4D). A fine structure of the object which is indicated in FIGS. 4B to 4D by a circle can be positioned such that it can be covered by the aperture blade 46 for all acquisition angles. Although this fine structure is not visible in FIG. 4B it leaves a footprint in scatter corrected image of FIG. 4C. In the reconstructed volumetric data of FIG. 4D it causes severe artifacts.

The impact of this problem can be effectively reduced by making the distances between holes smaller or by choosing an appropriate orientation for a given aperture plate 46. The orientation needs to be chosen such that for a given feature of the object under inspection regardless of its actual position there is a high probability that of this feature coincides not only once but as often as possible with any one of the apertures 48 when varying the projection angle. Hence identifying an appropriate orientation for a given aperture plate 46 means optimizing before mentioned probability. This approach not only applies to an aperture plate 46 with hexagonal geometry but to any given geometry of the aperture plate 46. In particular this approach could also be applied to an aperture plate 46 with rectangular geometry.

By way of example this effect can be addressed by the proposed preferred embodiment illustrated by means of FIG. 3. However as said before it can be addressed for any type of aperture plate. The preferred embodiment according to FIG. 3 comprises a specific orientation of the hexagonal grid relative to the common plane of relative rotation 100 of object 18 and the radiation source 12. In this embodiment one of the grid lines of the hexagonal grid can be inclined against the surface normal 102 of the common plane of rotation 100 by a defined inclination angle. Said inclination angle generally lies in the range of 0 to 15 degrees. In a more preferred embodiment the inclination angle can be in the range of 0 to 5 degrees. In certain embodiments the inclination angle can be equal to 0 degrees. This particular embodiment is shown in FIGS. 2 and 3.

Further, various other scatter rejection plates may be designed based on the specific imaging applications and requirements, so as to optimize scatter rejection performance. In certain embodiments, if the geometry of an x-ray setup can be fixed, focally aligned apertures 48 may be designed. This provides that no primary x-ray beam deflects at wide angles. In other words, the apertures 48 may be drilled at an angle parallel to the angle of incidence of the X-ray beam, so as to maximize the rejection of scatter radiation. Similarly, the aperture plate may be optimized for a particular X-ray energy application. Further, it should be noted that the spacing of the apertures 48 may be based on specific applications depending on cost and image quality requirements.

The flat panel VCT system 10 employs the scatter rejection plates 46 for generating initial scatter image of the object 18 in accordance with aspects of the present technique. For example, as illustrated in the schematic of FIG. 5, the VCT system 10 acquires a first projection image 56 of the object 18 without the scatter rejection plate 46. This first projection image 56 can include a primary (non-grid) image of the object as well as a scatter image of the object. The VCT system 10 then acquires a second projection image 58 of the object with the scatter rejection plate 46 positioned between the object 18 and the detector 16. This second projection image 58 can include only the primary image of the object 18. As will be appreciated by those skilled in the art, the primary image is free from any artifacts caused due to scatter radiation. Further, it should be noted that, in the second projection image, the primary image of the object 18 can be formed only at certain discrete locations where measurements can be obtained through the apertures 48 and can be therefore dependent on the type of scatter rejection plate 46 employed to acquire the image. The illustrated embodiment depicts the primary image acquired by using aperture plate 46. The first image 56 and the second projection image 58 may also be referred as non-grid image 56 and grid image 58 respectively.

The VCT system 10 then generates the scatter image of the object at the respective one of the projection angles based on the first projection image 56 and the second projection image 58. In particular, the processor 34 subtracts the second projection image 58 from the first projection image 56 to generate a scatter grid image 60. It should be noted that acquisition of the first projection image 56 and the second projection image 58, and the generation of scatter grid image 60 can be performed for each of the projection angles.

Figure 6:
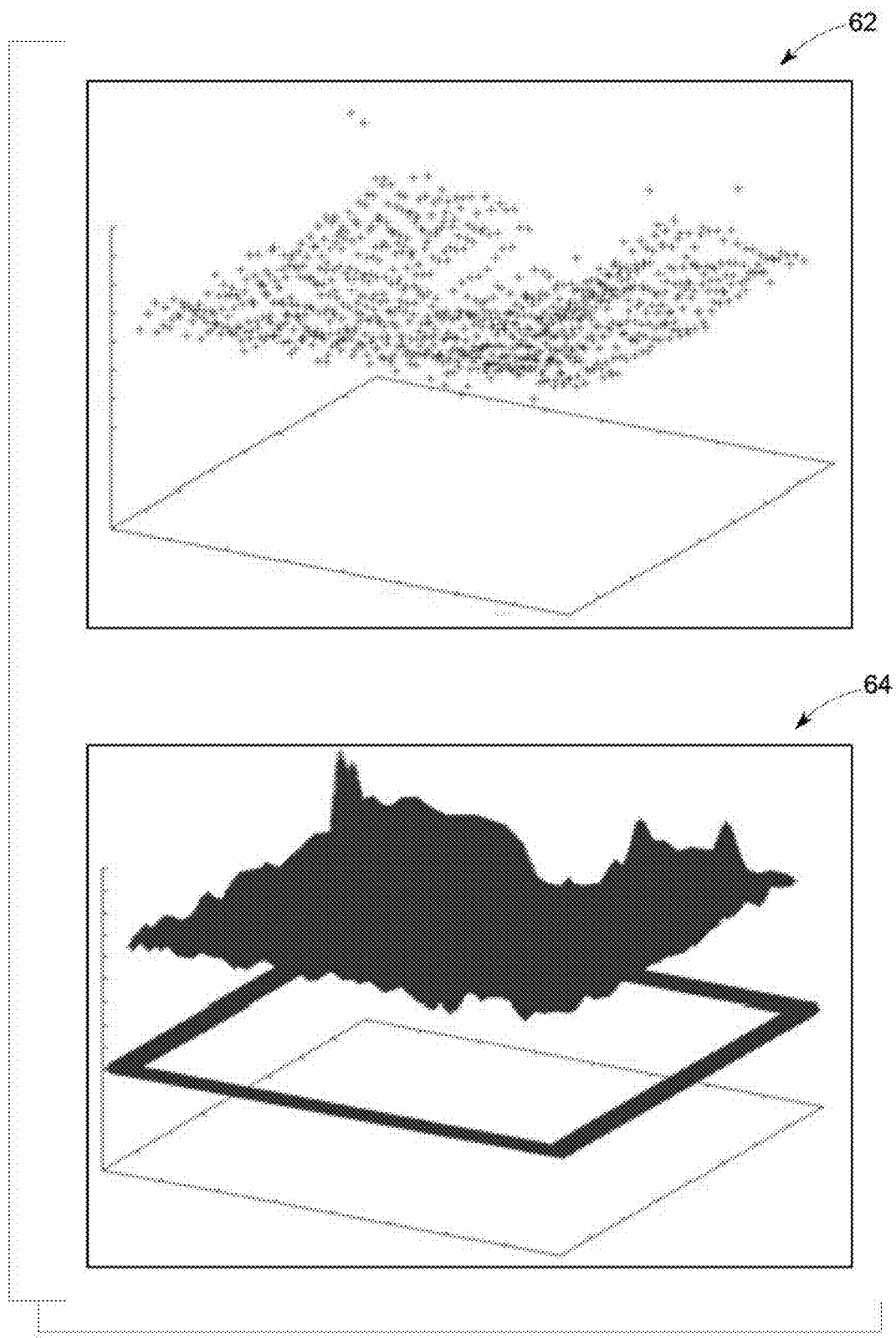
FIG. 6 depicts a schematic for interpolating the scatter grid image obtained by the technique of FIG. 5 to generate a complete scatter image in accordance with aspects of the present technique.

The generated scatter grid image 60 can then be interpolated to generate a complete scatter image. FIG. 6 depicts an example schematic for interpolating a scatter grid image obtained by the technique of FIG. 5 to generate a complete scatter image in accordance with aspects of the present technique. As illustrated, all aperture points or centroids for the scatter grid image can be first detected at step 62. It should be noted that, for the scatter grid image acquired by employing an aperture plate, the aperture points may be detected based on the required pixel resolution. The scatter grid image can then be interpolated based on the detected aperture points to generate a full or complete scatter image of the object at step 64. In other words, the data points can be first mapped to a regular grid and then interpolated using shape factors. As will be appreciated by those skilled in the art, any type of interpolation techniques may be employed to generate the scatter image from the scatter grid image. Non-limiting examples of the interpolation techniques include bi-linear interpolation, piecewise constant interpolation, bi-cubic interpolation, multivariate interpolation, and so forth.

As will be appreciated by those skilled in the art, a scatter image of the object can be generated for each of the projection angles. The generated scatter images can be stored in the memory for subsequent imaging. As will be appreciated by those skilled in the art, subsequent imaging can include acquiring projection images of the object from various projection angles and generating scatter free projection images for each projection angle based on the projection images and respective stored scatter images. The scatter free projection images can be generated by correcting the projection images based on respective ones of stored scatter images. In certain embodiments, the scatter free projection images may be corrected by subtracting the respective pre-stored scatter images from the acquired projection image for each of the projection angle. It should be noted that the orientation of the object during subsequent imaging should be substantially same as it was during generation of scatter image for each projection angles. The scatter free projection images may be further processed to normalize and correct for any bad pixels in the scatter free projection images. The generated or processed scattered free projection images may then be reconstructed to generate a three-dimensional image of the object. As will be appreciated by those skilled in the art, any suitable reconstruction technique may be employed for the image reconstruction. Non-limiting examples of the reconstruction techniques include filtered back projection (FBP), iterative filtered back projection (IFBP), iterative reconstruction and/or statistical reconstruction techniques.

The exemplary imaging system 10 may generate images of the object under examination by the techniques discussed herein. In particular, as will be appreciated by those of ordinary skill in the art, control logic and/or automated routines for performing the techniques and steps described herein may be implemented by the imaging system 10 of FIG. 1, by hardware, software, or combinations of hardware and software. For example, suitable code may be accessed and executed by the processor 34 to perform some or all of the techniques described herein. Similarly application specific integrated circuits (ASICs) configured to perform some or all of the techniques described herein may be included in the processor 34 and/or the system controller 22.

Figure 7:
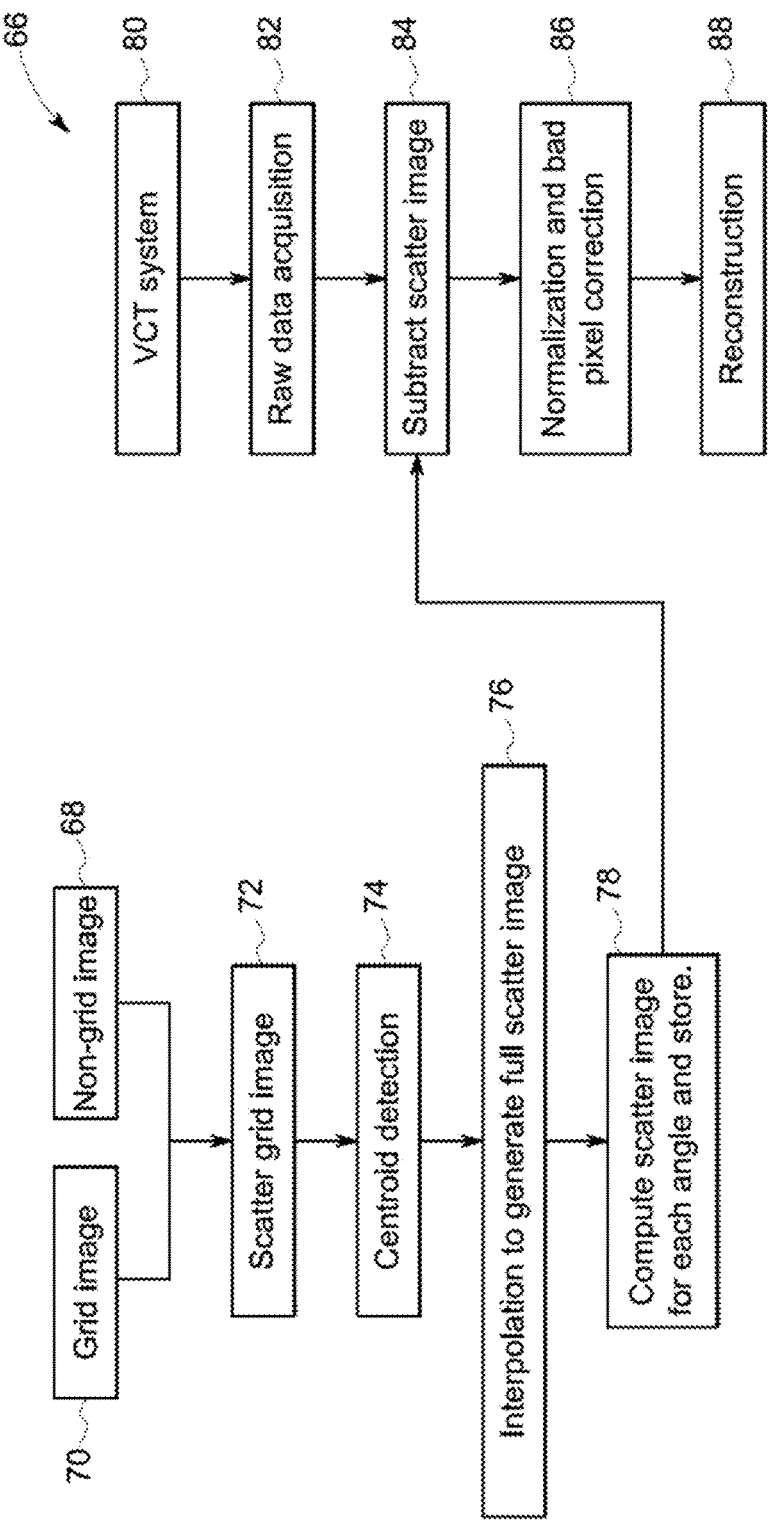
FIG. 7 depicts a control logic for inspecting an object via the flat panel VCT system of FIG. 1 by employing a scatter measurement and correction technique in accordance with aspects of the present technique.

For example, referring now to FIG. 7, exemplary control logic for inspecting an object by employing scatter measurement and correction technique on the imaging system such as flat panel VCT system 10 is depicted in accordance with aspects of the present technique. As illustrated in the flowchart 66, a non-grid image and a grid image may be acquired for a given object at multiple projection angles via the VCT system at steps 68 and 70 respectively. As discussed above, the grid image may be acquired by employing the scatter rejection plate positioned between the object and the detector. A scatter grid image can then be generated based on the non-grid image and the grid image at step 72. The scatter grid image can then be processed to detect multiple aperture points or centroids at step 74. Based on the detected centroids, the scatter grid image can then be interpolated to generate a full scatter image of the given object at step 76. The process can be repeated for each of the multiple projection angles and the generated scatter images for the respective projection angles can be stored for subsequent imaging applications at step 78.

During subsequent imaging, the VCT system images the object at step 80 and acquires projection images of the object from various projection angles at step 82. It should be noted that, the projection images can be acquired for same projection angles for which the scatter images have been generated. The scatter free projection images can then be generated based on the projection images and corresponding scatter images at step 84. In one embodiment this can be done by subtracting the corresponding scatter images from the acquired projection images. The scatter free projection images can then be post processed at step 86. The post processing may involve normalization and correction for bad pixels. The processed scatter free projection images can then be reconstructed to generate a three-dimensional image of the object at step 88.

Figure 8:
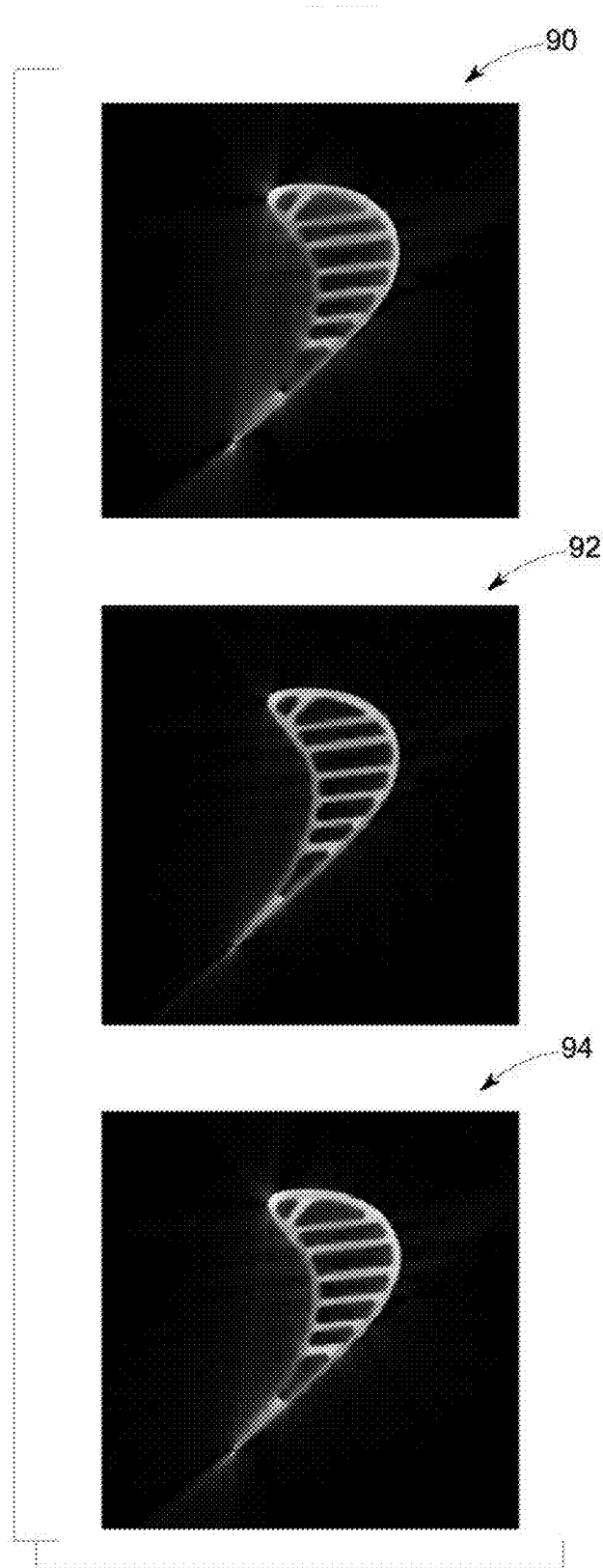
FIG. 8 depicts, for a turbine fan blade, uncorrected image and scatter corrected images by employing the control logic of FIG. 7.

FIG. 8 illustrates, for a turbine fan blade, uncorrected image and scatter corrected images by employing control logic of FIG. 7. Image 90 is the uncorrected image obtained by a typical VCT system, while images 92 and 94 are scatter corrected images obtained by employing the scatter rejection plate and the control logic described via the flowchart 66. Further, it should be noted that image 92 is the scatter corrected image obtained by employing an aperture plate.

It should be noted that one or more imaging parameters should be substantially maintained (that is, maintained at substantially similar values) for a particular imaging application and inspection requirement. Non-limiting examples of the imaging parameters include a type of object being imaged, a shape and an orientation of the object being imaged, projection angles from which the scatter images and subsequent projection images are acquired, an x-ray technique being employed, a geometry and one or more settings of the source and the detector, distance of the scatter rejection plates from the source and the detector, and so forth. For example, the above process may be set for imaging similar objects (e.g., turbine blades). The objects should be mounted on the turntable at substantially similar orientations. Further, the distance of the scatter rejection plate from the source and the detector should be substantially maintained while acquiring and storing the scatter images for each of the predetermined projection angles. In one embodiment, this may be achieved by coupling or attaching the scatter rejection plate to the two-dimensional flat panel detector array. Additionally, projection images should be acquired for projection angles for which the scatter images have been generated and stored. Moreover, the x-ray technique employed, the geometry and other settings for the source and the detector should be maintained at substantially similar values, such that the beam shape and intensity can be same for various image acquisitions.

Figure 9A:
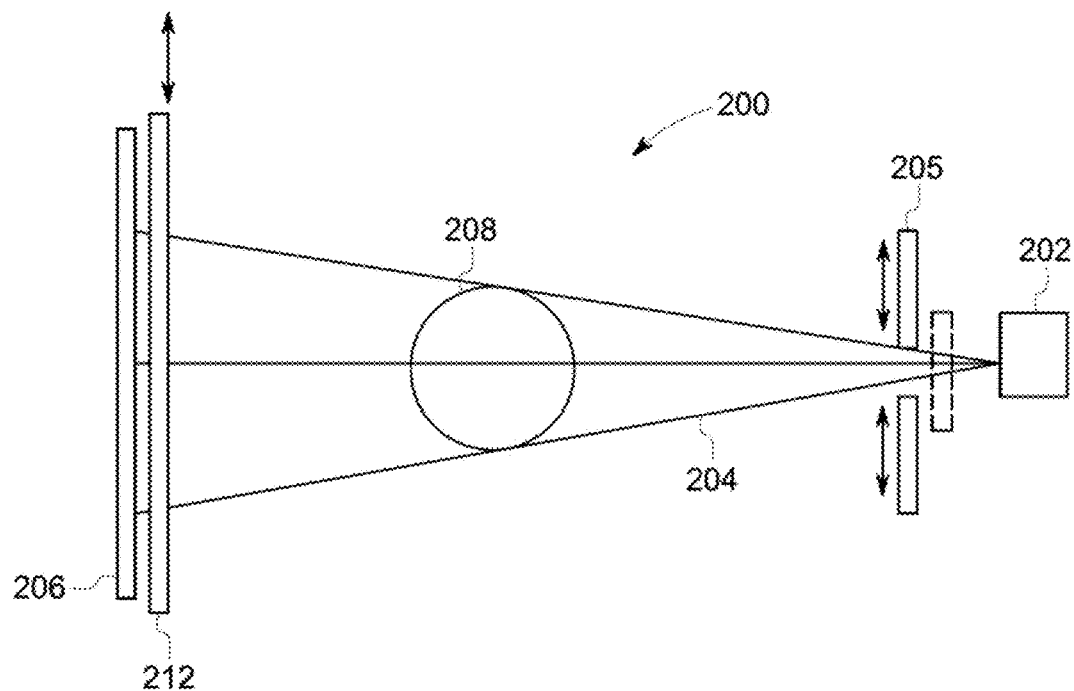
FIG. 9A depicts a top view schematic of a CT imaging system.
Figure 9B:
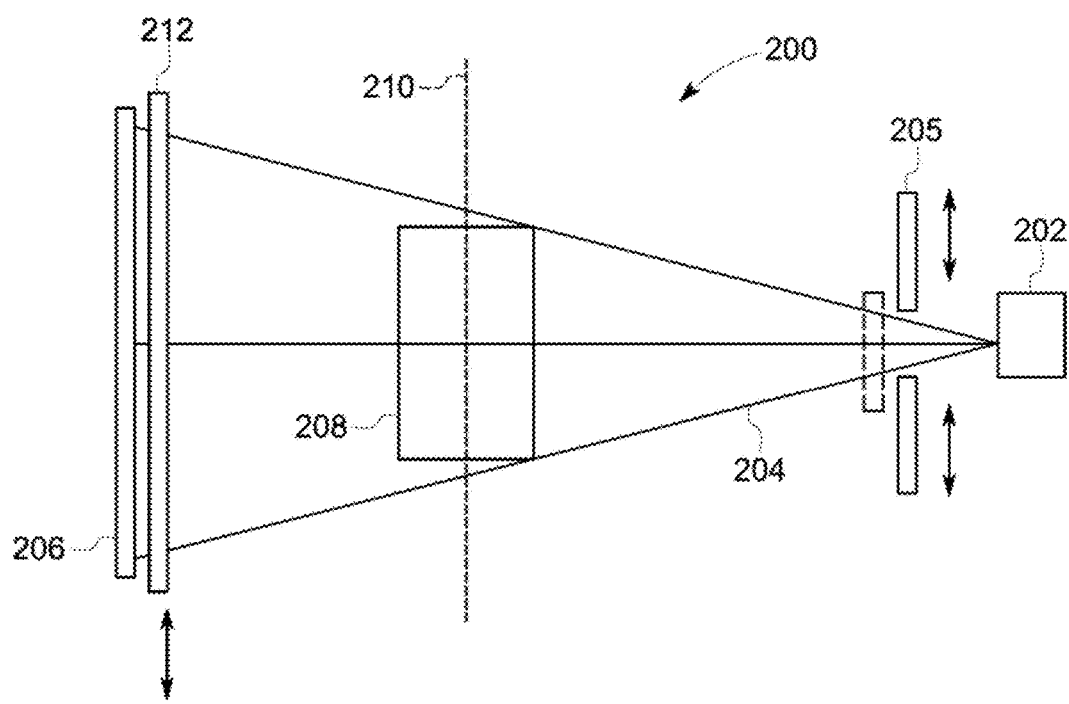
FIG. 9B depicts a side view schematic of the CT imaging system of FIG. 9A.

Referring now to FIGS. 9A-9B, another imaging system 200 for use in accordance with an imaging technique to produce a high resolution image described herein is illustrated. In the illustrated embodiment, the imaging system 200 can be a volumetric computed tomography (VCT) system designed both to acquire image data and to process the image data for display and analysis in accordance with a present technique. In the illustrated embodiment, the imaging system 200 can include a radiation source 202, such as an X-ray source 202. A collimator 205 may be positioned adjacent to the radiation source 202 for regulating the size and shape of the stream of radiation 204 that emerges from the radiation source 202.

The stream of radiation 204 can be projected toward a detector array 206 placed on the opposite side of the radiation source 202, relative to an object 208 that is to be imaged. The stream of radiation 204 passes into an imaging volume in which the object 208 to be imaged, such as a turbine blade or other item to be imaged, may be positioned. A portion of the radiation 204 passes through or around the object 208 and impacts the detector array 206. The detector array 206 can be generally formed as a two-dimensional array of detection elements.

The object 208, radiation source 202, and detector array 206 can be typically displaced relative to each other, allowing projection data to be acquired at various views relative to the object 208 if desired. In an example, the object 208 can be positioned on a table, such as a turntable, so that the object 208 may be rotated about a rotation axis 210. Data collected from the detector array 206 typically undergoes pre-processing to condition the data to represent the line integrals of the attenuation coefficients of the scanned object 208. The processed data or projections can then be reconstructed to formulate a volumetric image of the scanned area, as discussed in greater detail above.

The imaging system 200 may employ a variety of scatter mitigation and/or correction techniques for improving the image quality and resolution. For example, as discussed above, a scatter rejecting aperture plate 212 for rejecting the scatter radiation resulting from the object 208 as well as those resulting from the background can be employed. As illustrated in this embodiment, in order to further improve the resolution and image quality, the aperture plate 212 can be movable between a plurality of positions. These positions will be described further below with regard to FIGS. 10A-10D. By moving the aperture plate 212 between the plurality of positions, smaller structures on the object 208 can be recognized and artifacts can be better avoided.

As discussed above with regard to FIGS. 2-3, the aperture plate 212 can include a plurality of sub-centimeter sized apertures 48, such as circular apertures, drilled in a plate. The apertures 48 can be positioned on a two-dimensional grid. The two-dimensional grid in this embodiment can have any geometric shape, such as a circular shape, rectangular shape, or hexagonal shape, among others. In certain embodiments, the circular apertures 48 may be about 1-2 millimeters in diameter spaced apart at about 5 millimeters from each other (center-to-center).

Figure 10A:
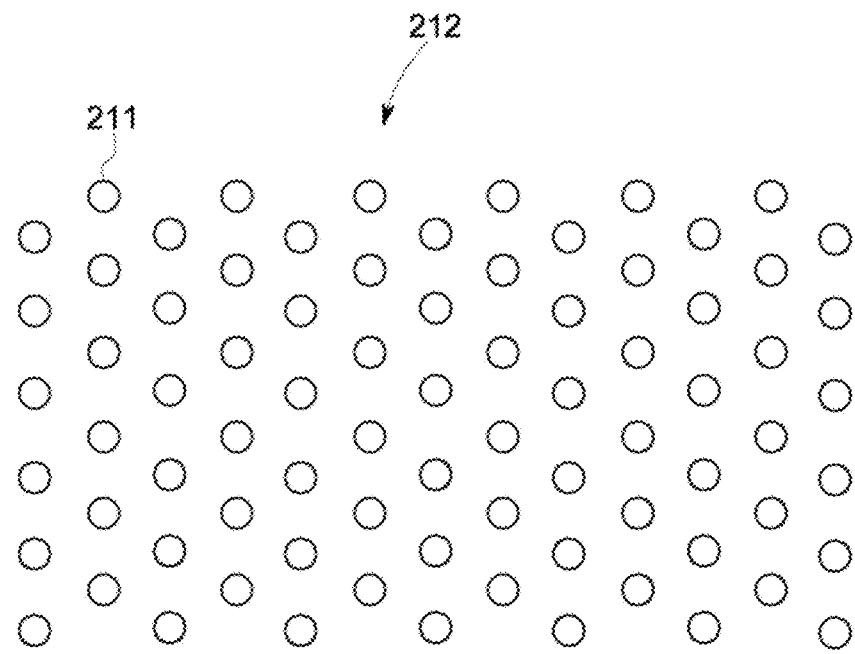
FIGS. 10A-10D are positional diagrams for the apertures of the aperture plates.
Figure 10B:
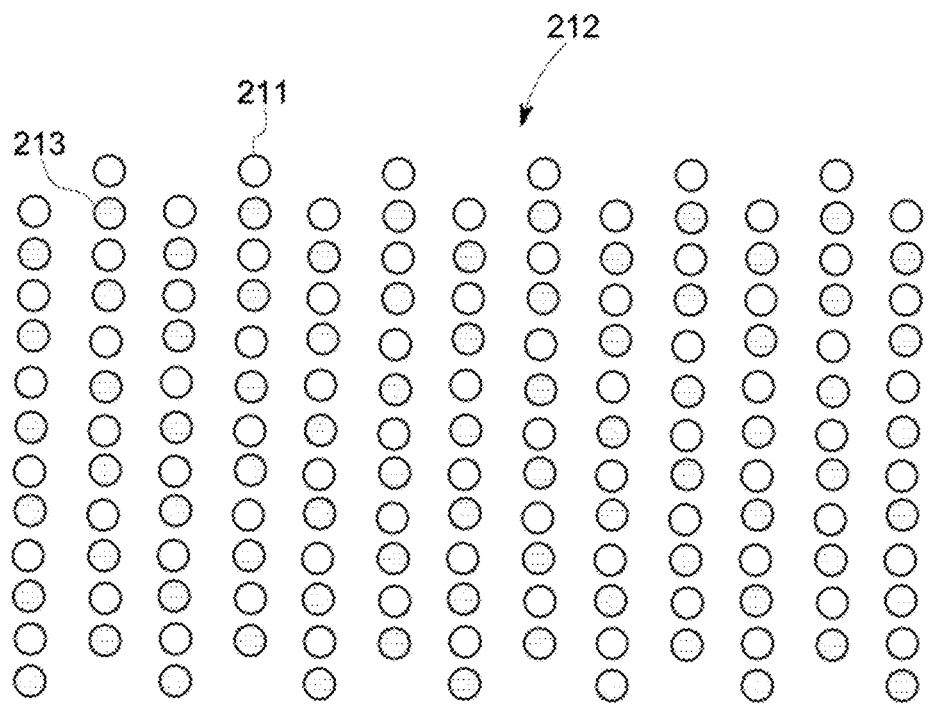
Figure 10C:
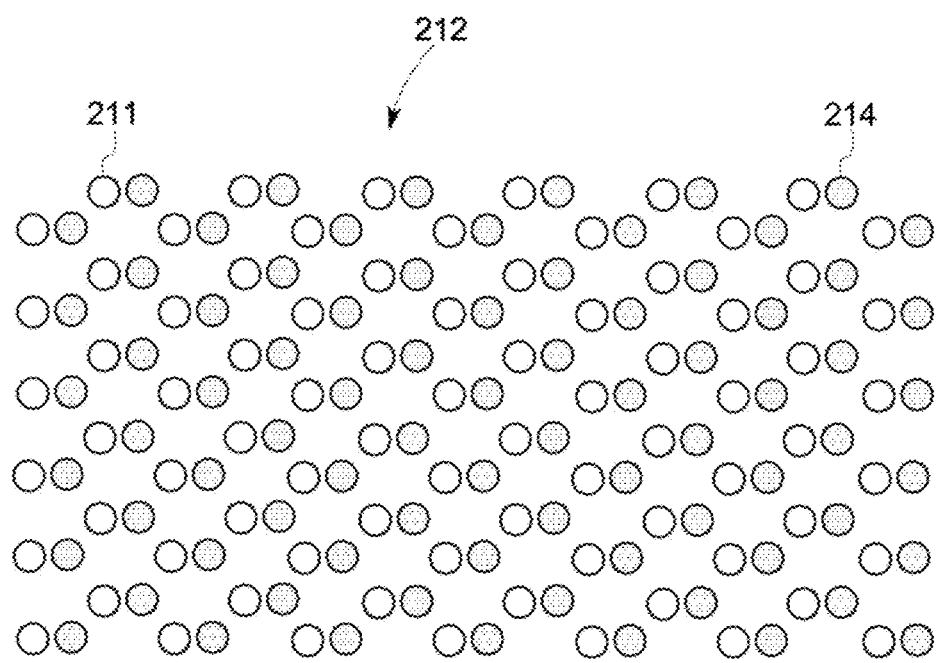
Figure 10D:
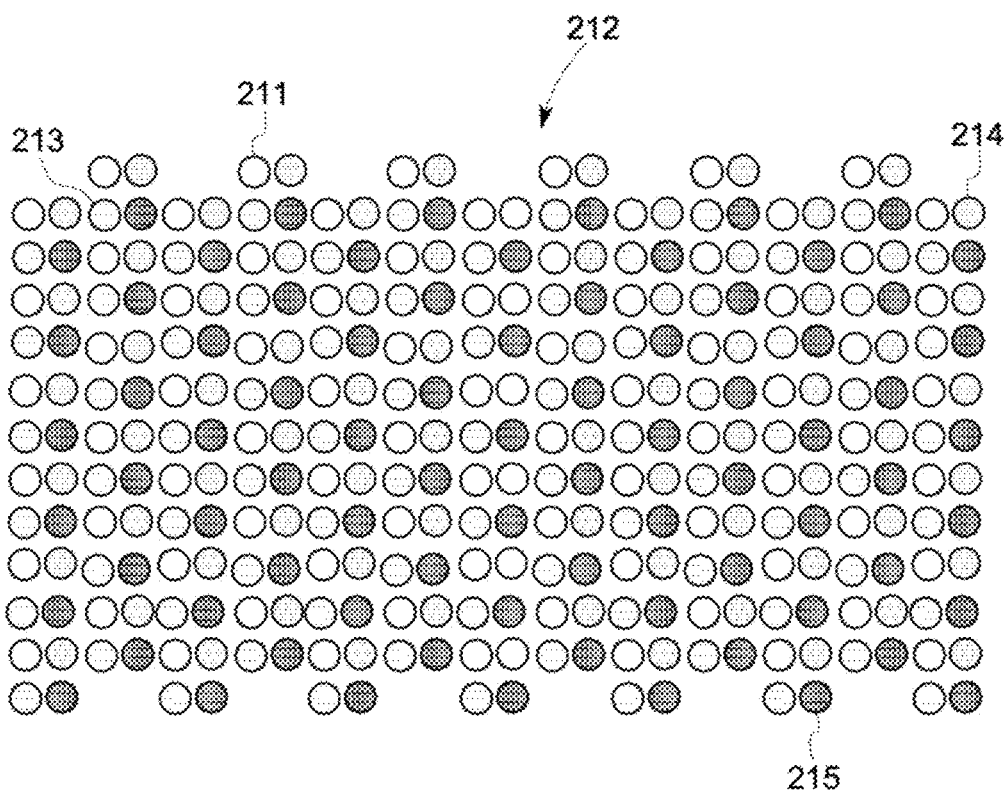

Referring now to FIGS. 10A-D, as discussed above, the aperture plate 212 can be movable between a plurality of positions in order to increase the resolution and quality of the generated image. As illustrated in FIG. 10A, the aperture plate 212 can initially be placed in a first position 211. After a first grid image is gathered, the aperture plate 212 can be repositioned to a secondary position 213, 214 and a second grid image gathered. In an embodiment, the aperture plate 212 can be moved uni-directionally. For example, the aperture plate 212 can be moved vertically from the first position 211 to the second position 213, as illustrated in FIG. 10B, and a second image gathered or the aperture plate 212 can be moved horizontally from the first position 211 to the third position 214, as illustrated in FIG. 10C, and the second image gathered. In another embodiment, the aperture plate 212 can be moved bi-directionally. For example, the aperture plate 212 can be moved both vertically and horizontally, as illustrated in FIG. 10D. In this embodiment, the aperture plate 212 can be placed in a first position 211 and a first image gathered, moved to a second position 213 and a second image gathered, moved to a third position 214 and a third image gathered, and moved to a fourth position 215 and a fourth image gathered. In another embodiment, the aperture plate 212 can be rotated relative to the object 208. An image can be gathered at each position 211, 213, 214, 215 of the aperture plate 212.

In another embodiment, resolution of the image can also be increased by moving the object 208 in front of the grid of the aperture plate 212. Similar to repositioning the aperture plate 212, discussed above, in this embodiment the sample can be moved uni-directionally, bi-directionally, or rotated, for example. By repositioning the apertures 48 of the aperture plate 212 relative to the object 208, the resolution of the image can be increased. The aperture plate 212 and/or object 208 can be repositioned manually or automatically.

The resolution of the image can be determined by the number of positions at which the aperture plate 212 and/or object 208 can be placed. As the number of positions increases, the resolution of the image also increases. For example, using bi-directional movement of the aperture plate 212, positioning the aperture plate 212 in four positions increases the image resolution by a factor of two (2). In another example, positioning the aperture plate 212 in sixteen positions increases the image resolution by a factor of four (4). This improvement in image resolution by repositioning the aperture plate 212 is illustrated by FIGS. 11A-11B.

Figure 11A:
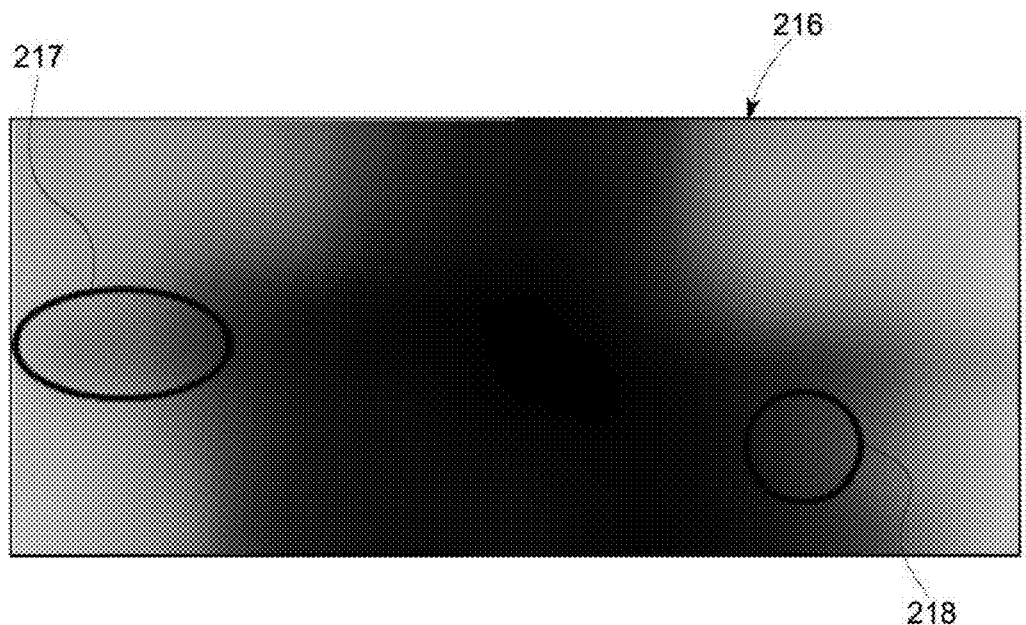
FIG. 11A is a scatter corrected CT image.
Figure 11B:
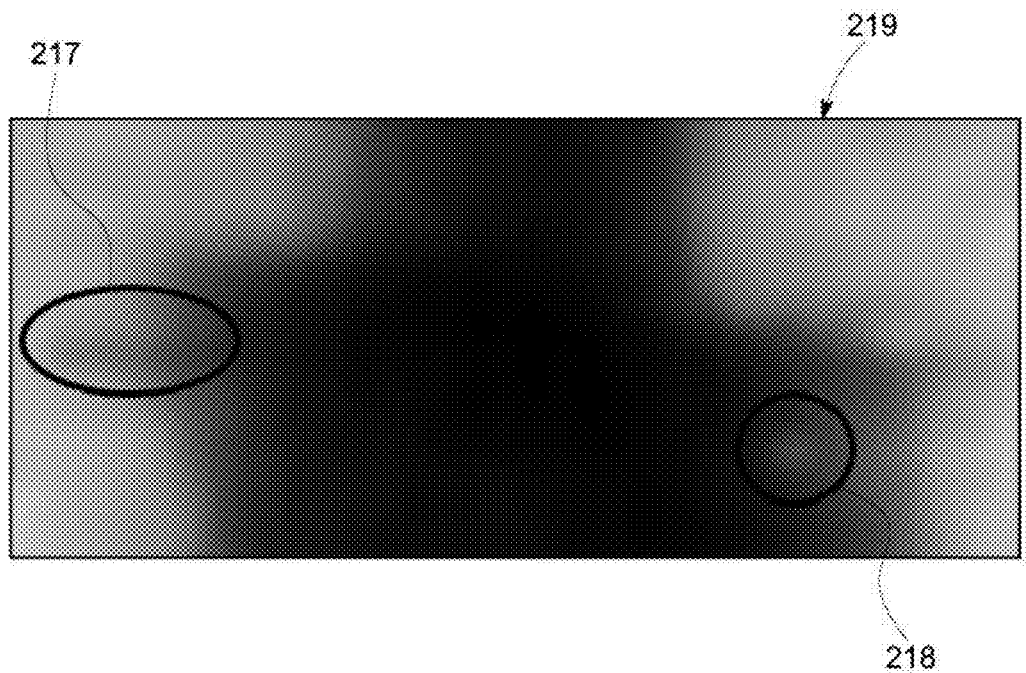
FIG. 11B is a multi-position scatter corrected CT image.

FIG. 11A illustrates an image 216 of the object 208 generated in which the aperture plate 212 was placed in a single position. FIG. 11B illustrates an image 219 of the object 208 in which the aperture plate 212 was placed in four positions during gathering of the data. As illustrated by the first 217 and second 218 location indicated in these figures, the additional positions of the aperture plate 212 results in an image in FIG. 11B in which additional details are visible at each of the first location 217 and the second location 218 as compared to FIG. 11A.

Figure 12:
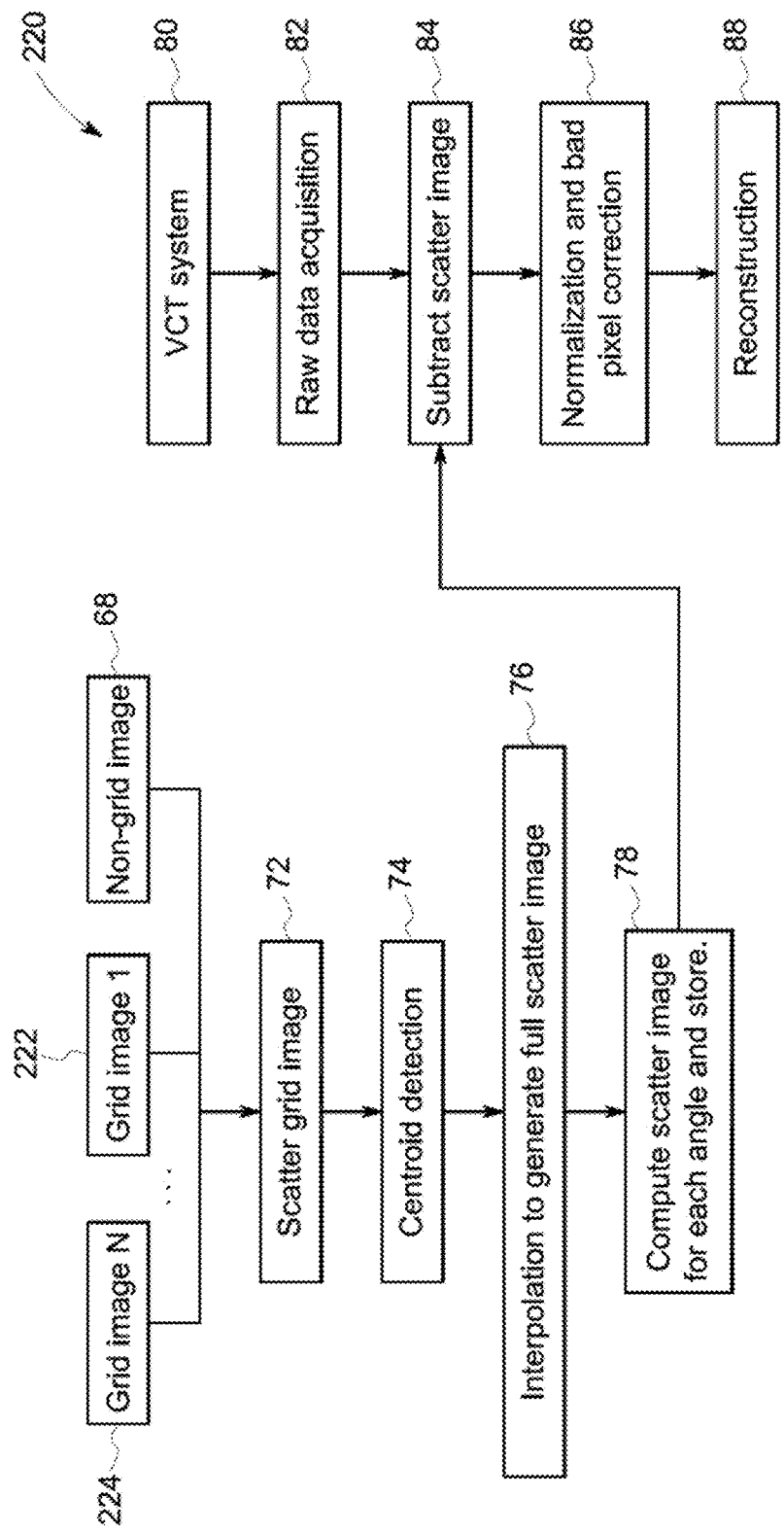
FIG. 12 is a flow diagram of an exemplary method for imaging an object.

Referring now to FIG. 12, a flowchart illustrating an exemplary method 220 of imaging an object, such as the object 208, by employing an advanced scatter measurement and correction technique on the imaging system 200 is depicted. This method is exemplary only and the blocks may be altered, added, removed, and/or rearranged. As illustrated in the flowchart, at block 68, a primary, non-grid image can be acquired for the object 208 at multiple projection angles via the imaging system 200. At block 222, a first grid image can be acquired. The first grid image can be acquired by employing the scatter rejection aperture plate 212 positioned between the object 208 and the detector 206. Following acquisition of the first grid image, the apertures 48 of the aperture plate 212 can be repositioned relative to the object 208 and an additional image can be acquired at block 224. For example, the aperture plate 212 can be moved to a second position and the additional grid image can be acquired with the aperture plate 212 at the additional position. In another example, the object 208 can be moved between positions while the aperture plate 212 remains stationary. The aperture plate 212 and/or the object 208 can be moved to a plurality of positions and a grid image acquired at each of the plurality of positions. The number of positions can be determined based on the level of resolution desired in the final image.

As discussed above, the aperture plate 212 can be moved uni-directionally (e.g., horizontally or vertically), bi-directionally (e.g., horizontally and vertically), rotated, etc. The aperture plate 212 and/or the object 208 can be moved manually or automatically between the positions.

Following acquisition of the plurality of grid images, at block 72, a scatter grid image can be generated based on the non-grid image and the plurality of grid images. The scatter grid image can then be processed to detect multiple aperture points or centroids at block 74. Based on the detected centroids, the scatter grid image can then be interpolated to generate a full scatter image of the object 208 at block 76. The process can be repeated for each of the projection angles and the generated scatter images for the respective projection angles can be stored for subsequent imaging applications at block 78.

At block 80, the imaging system 200 images the object 208 and acquires projection images of the object from various projection angles at block 82. At block 84, the scatter free projection images can be generated based on the projection images and corresponding scatter images. In an embodiment, this can be done by subtracting the corresponding scatter images from the acquired projection images. At block 86, the scatter free projection images can be post processed. The post processing may involve normalization and correction for bad pixels. At block 88, the processed scatter free projection images can then be reconstructed to generate a three-dimensional image of the object 208.

As will be appreciated by those skilled in the art, the scatter correction techniques described in the various embodiments discussed above permit a measurement of the scatter content in the projection images used for VCT imaging and correct the projection images, thereby improving the VCT image quality. The technique permits measurement of scatter content in x-ray images for a given geometry, scanning orientation, and x-ray technique prior to a VCT scan and use it during an actual imaging scan. This improves the throughput of the VCT system since scatter correction for the projection images is then a simple image subtraction process. Further, as will be appreciated by those skilled in the art, it is easier to measure primary radiation than the scatter radiation and positioning the scatter rejection plate between the object and the detector makes the measurement of primary radiation substantially convenient. Additionally, the use of narrow collimators permits the imaging of the higher spatial frequency content of the scatter images. Moreover, the technique permits capture and correction of the beam scatter (scatter due to the imaged object) as well as the background radiation scatter (scatter due to external object).

Further, as will be appreciated by those skilled in the art, the technique may be employed as a part of the system calibration process prior to the actual imaging application. Typically, prior to performing VCT imaging for metrology or inspection, an operator has to perform a few system calibration steps such as, flat field calibration of the detector, bad pixel test and calibration of the detector, geometrical alignment and calibration of the system. The scatter correction technique described in the embodiments discussed above may similarly become a part of the calibration process where the scatter images will be obtained for a specific object and stored prior to the performance of an actual metrology or inspection process.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for generating a scatter image of an object at a projection angle in an imaging system, the method comprising:
   a. acquiring a non-grid image of the object using a radiation source and a detector;
   b. positioning a scatter rejecting aperture plate between the object and the detector at a first position, wherein the scatter rejecting aperture plate comprises a plurality of apertures, said plurality of apertures being positioned on a grid;
   c. acquiring a first grid image of the object with the scatter rejecting aperture plate disposed between the object and the detector at the first position;
   d. moving the scatter rejecting aperture plate to a second position between the object and the detector;
   e. acquiring a second grid image of the object with the scatter rejecting aperture plate disposed between the object and the detector at the second position;
   f. generating a scatter image of the object based on the non-grid image, the first grid image, and the second grid image; and
   g. storing the scatter image of the object.

2. The method of claim 1, further comprising moving the scatter rejecting aperture plate to at least a third position between the object and the detector; acquiring at least a third grid image of the object with the scatter rejecting aperture plate disposed between the object and the detector at the third position; and generating the scatter image of the object based on the non-grid image, the first grid image, the second grid image, and the at least third grid image.

3. The method of claim 1, wherein moving the scatter rejecting aperture plate comprises moving the scatter rejecting aperture plate uni-directionally.

4. The method of claim 3, wherein moving the scatter rejecting aperture plate uni-directionally comprises moving the scatter rejecting aperture plate at least one of horizontally and vertically.

5. The method of claim 1, wherein moving the scatter rejecting aperture plate comprises moving the scatter rejecting aperture plate bi-directionally.

6. The method of claim 5, wherein moving the scatter rejecting aperture plate bi-directionally comprises moving the scatter rejecting aperture plate horizontally and vertically.

7. The method of claim 1, wherein moving the scatter rejecting aperture plate comprises rotating the scatter rejecting aperture plate.

8. The method of claim 1, wherein a three-dimensional image of the object is generated based on the scatter image and wherein resolution of the three-dimensional image of the object is dependent on a plurality of scatter rejecting aperture plate positions.

9. The method of claim 8, wherein increasing the number of scatter rejecting aperture plate positions increases the resolution of the three-dimensional image of the object.

10. The method of claim 1, further comprising automatically moving the scatter rejecting aperture plate between positions.

11. The method of claim 1, wherein the scatter rejecting aperture plate has a shape selected from the group comprising hexagonal, rectangular, and circular.

12. A method for generating a three-dimensional image of an object, the method comprising:
   a. acquiring a plurality of projection images of the object using a source and a detector oriented at a plurality of projection angles relative to the object; said plurality of projection angles being realized by relatively rotating the object and the radiation source in a common plane of rotation;
   b. acquiring a scatter image at each of the plurality of projection angles, wherein acquiring each scatter image comprises
      i. acquiring a non-grid image of the object using a radiation source and a detector,
      ii. positioning a scatter rejecting aperture plate between the object and the detector at a first position, wherein the scatter rejecting aperture plate comprises a plurality of apertures, said plurality of apertures being positioned on a grid,
      iii. acquiring a first grid image of the object with the scatter rejecting aperture plate disposed between the object and the detector at the first position,
      iv. repositioning the scatter rejecting aperture plate to a second position between the object and the detector,
      v. acquiring a second grid image of the object with the scatter rejecting aperture plate disposed between the object and the detector at the second position, and
      vi. generating a scatter image of the object based on the non-grid image, the first grid image, and the second grid image;
   c. generating a plurality of scatter free projection images by correcting the plurality of projection images based on respective ones of a plurality of stored scatter images by subtracting the scatter images from the respective projection images in a single process step; and d. reconstructing a three-dimensional image of the object based on the scatter free projection images.

13. The method of claim 12, wherein repositioning the scatter rejecting aperture plate comprises moving the scatter rejecting aperture plate from a first position to at least a second position between the object and the detector.

14. The method of claim 13, wherein moving the scatter rejecting aperture plate comprises one selected from the group comprising moving the scatter rejecting aperture plate uni-directionally, moving the scatter rejecting aperture plate bi-directionally, and rotating the scatter rejecting aperture plate.

15. The method of claim 12, wherein repositioning the scatter rejecting aperture plate comprises moving the sample from a first position to at least a second position in front of the scatter rejecting aperture plate.

16. The method of claim 15, wherein moving the sample comprises one selected from the group comprising moving the sample uni-directionally, moving the sample bi-directionally, and rotating the sample.

17. A volumetric CT system for imaging an object configured to generate a scatter free image of an object for use in generating a three-dimensional image of the object, the system comprising:

a. a source and a detector configured to move with respect to the object, the detector configured to acquire a plurality of images of the object;

b. an aperture plate configured to be positioned at a plurality of positions between the object and the detector, the aperture plate comprising a plurality of apertures, said apertures being positioned on a grid; and c. a processor configured to acquire a non-grid image of the object without the aperture plate and a grid image of the object with the aperture plate at each of the plurality of positions between the object and the detector and generate the scatter image of the object based on the non-grid images and the grid images acquired at each of the plurality of positions.

18. The system of claim 17, wherein resolution of the three-dimensional image of the object is dependent on a number of positions of the aperture plate at each projection angle and wherein the resolution of the three-dimensional image of the object increases as the number of positions of the aperture plate at each projection angle increases.

19. The system of claim 17, wherein repositioning the aperture plate comprises one selected from the group comprising moving the aperture plate from a first position to at least a second position between the object and the detector and moving the sample from a first position to at least a second position in front of the aperture plate.

20. The system of claim 19, wherein moving the aperture plate or the sample comprises one selected from the group comprising moving the aperture plate or the sample uni-directionally, moving the aperture plate or the sample bi-directionally, and rotating the aperture plate or the sample.

* * * * *